United States Patent
Rim et al.

(10) Patent No.: US 10,527,556 B2
(45) Date of Patent: Jan. 7, 2020

(54) OPTICAL MEASURING METHOD AND APPARATUS, AND METHOD OF MANUFACTURING SEMICONDUCTOR DEVICE USING THE SAME

(71) Applicant: SAMSUNG ELECTRONICS CO., LTD., Suwon-si, Gyeonggi-do (KR)

(72) Inventors: Min-Ho Rim, Hwaseong-si (KR); Jung-Soo Kim, Hwaseong-si (KR); Young-Hoon Sohn, Incheon (KR); Yu-Sin Yang, Seoul (KR); Chung-Sam Jun, Suwon-si (KR); Yun-Jung Jee, Seongnam-si (KR)

(73) Assignee: SAMSUNG ELECTRONICS CO., LTD., Suwon-si, Gyeonggi-Do (KR)

( * ) Notice: Subject to any disclaimer, the term of this patent is extended or adjusted under 35 U.S.C. 154(b) by 0 days.

(21) Appl. No.: 15/795,592

(22) Filed: Oct. 27, 2017

(65) Prior Publication Data
US 2018/0340894 A1 Nov. 29, 2018

(30) Foreign Application Priority Data
May 24, 2017 (KR) .................. 10-2017-0064008

(51) Int. Cl.
*G01N 21/88* (2006.01)
*H01L 21/28* (2006.01)
(Continued)

(52) U.S. Cl.
CPC ..... *G01N 21/8806* (2013.01); *G01N 21/9501* (2013.01); *G02B 27/0944* (2013.01); *G02B 27/0988* (2013.01); *G06T 7/001* (2013.01); *H01L 22/12* (2013.01); *H01L 27/11556* (2013.01); *H01L 29/40114* (2019.08);
(Continued)

(58) Field of Classification Search
CPC ......... H01L 22/10–14; H01L 22/20–26; H01L 22/30–34; H01L 27/11582; H01L 22/12; H01L 21/28273; H01L 27/11556; H01L 21/28282; G01R 1/0491; G01N 21/9505; G01N 21/9501; G01N 2223/6116; G01N 21/95; G01N 21/9503; G01N 21/8806; G01N 2201/063; G01N 2201/061; H01S 5/0014–0042; B82Y 35/00; B81C 99/003–0055; G06T 7/001; G06T 2207/30148; G02B 27/0972; G02B 27/0927; G02B 27/0944; G02B 27/0988; G02B 5/001
See application file for complete search history.

(56) References Cited

U.S. PATENT DOCUMENTS 4,887,885 A 12/1989 Durnin et al.
5,336,875 A 8/1994 Ono et al.
(Continued)

FOREIGN PATENT DOCUMENTS

JP 2009-109628 5/2009

*Primary Examiner* — Sonya D. McCall-Shepard
(74) *Attorney, Agent, or Firm* — F. Chau & Associates, LLC

(57) ABSTRACT

An optical measuring method includes generating a Bessel beam, filtering the Bessel beam to generate a focused Bessel beam, vertically irradiating the focused Bessel beam onto a substrate in which an opening is formed, and detecting light reflected from the substrate to obtain an image of a bottom surface of the opening.

17 Claims, 13 Drawing Sheets

(51) Int. Cl.

| | |
|---|---|
| *G01N 21/95* | (2006.01) |
| *G06T 7/00* | (2017.01) |
| *H01L 27/11556* | (2017.01) |
| *H01L 21/66* | (2006.01) |
| *G02B 27/09* | (2006.01) |
| *H01L 27/11582* | (2017.01) |
| *G02B 5/00* | (2006.01) |

(52) U.S. Cl.
CPC .. *H01L 29/40117* (2019.08); *G01N 2201/061* (2013.01); *G01N 2201/063* (2013.01); *G06T 2207/30148* (2013.01); *H01L 27/11582* (2013.01)

(56) References Cited

U.S. PATENT DOCUMENTS

| | | | |
|---|---|---|---|
| 5,583,342 A * | 12/1996 | Ichie | G02B 5/001 250/458.1 |
| 6,970,253 B2 | 11/2005 | Lindner et al. | |
| 7,009,712 B2 | 3/2006 | Hill | |
| 7,362,428 B2 | 4/2008 | Chang et al. | |
| 8,873,067 B2 | 10/2014 | Lee et al. | |
| 9,140,539 B2 | 9/2015 | Scheiner | |
| 9,305,341 B2 | 4/2016 | Claypool | |
| 2011/0304723 A1 * | 12/2011 | Betzig | G02B 21/002 348/79 |
| 2014/0300890 A1 * | 10/2014 | Lange | G01N 21/9501 356/51 |
| 2015/0299018 A1 | 10/2015 | Bhuyan et al. | |
| 2018/0149603 A1 * | 5/2018 | Bhattacharyya | G01N 21/9505 |

\* cited by examiner

146

OPTICAL MEASURING METHOD AND APPARATUS, AND METHOD OF MANUFACTURING SEMICONDUCTOR DEVICE USING THE SAME

CROSS-REFERENCE TO RELATED APPLICATION

This application claims priority under 35 U.S.C. § 119 to Korean Patent Application No. 10-2017-0064008 filed on May 24, 2017 in the Korean Intellectual Property Office, the disclosure of which is incorporated by reference herein in its entirety.

TECHNICAL FIELD

Exemplary embodiments of the present inventive concept relate to an optical measuring method and apparatus, and more particularly to a method of manufacturing a semiconductor device using the same.

DISCUSSION OF RELATED ART

In a method for manufacturing a semiconductor device such as a DRAM or a vertical-type NAND memory device, or a semiconductor package such as a stack chip package using a through silicon via (TSV), a process for forming high aspect ratio openings may be performed. Bottom surfaces of the openings may be difficult to accurately measure or inspect using a non-destructive method.

SUMMARY

According to an exemplary embodiment of the present inventive concept, an optical measuring method includes generating a Bessel beam, and filtering the Bessel beam to generate a focused Bessel beam. The method includes directing the focused Bessel beam into an opening formed in a substrate along a direction orthogonal to an upper surface of the substrate. The method includes detecting light reflected from a bottom surface of the opening to obtain an image of the bottom surface of the opening.

According to an exemplary embodiment of the present inventive concept, an optical measuring apparatus includes a stage configured to support a substrate having an opening formed therein. A Bessel beam generator is configured to generate a Bessel beam from an illumination optical source. A Bessel beam adjuster is in a path of the Bessel beam. The Bessel beam adjuster is configured to filter the Bessel beam to generate a focused Bessel beam. A beam splitter is configured to direct the focused Bessel beam to the substrate on the stage. An optical detector is configured to detect light reflected from the substrate to obtain an image of a bottom surface of the opening.

According to an exemplary embodiment of the present inventive concept, a method of manufacturing a semiconductor device includes providing a wafer including an opening. The method includes generating a Bessel beam and filtering the Bessel beam to generate a focused Bessel beam. The method includes directing the focused Bessel beam into the opening along a direction orthogonal to an upper surface of the wafer. The method includes detecting light reflected from the wafer to obtain an image of a bottom surface of the opening and analyzing the obtained image to detect a defect of the opening.

BRIEF DESCRIPTION OF THE DRAWINGS

The above and other features of the present inventive concept will become more apparent by describing in detail exemplary embodiments thereof with reference to the accompanying drawings, in which.

DETAILED DESCRIPTION OF THE EMBODIMENTS

Figure 1:
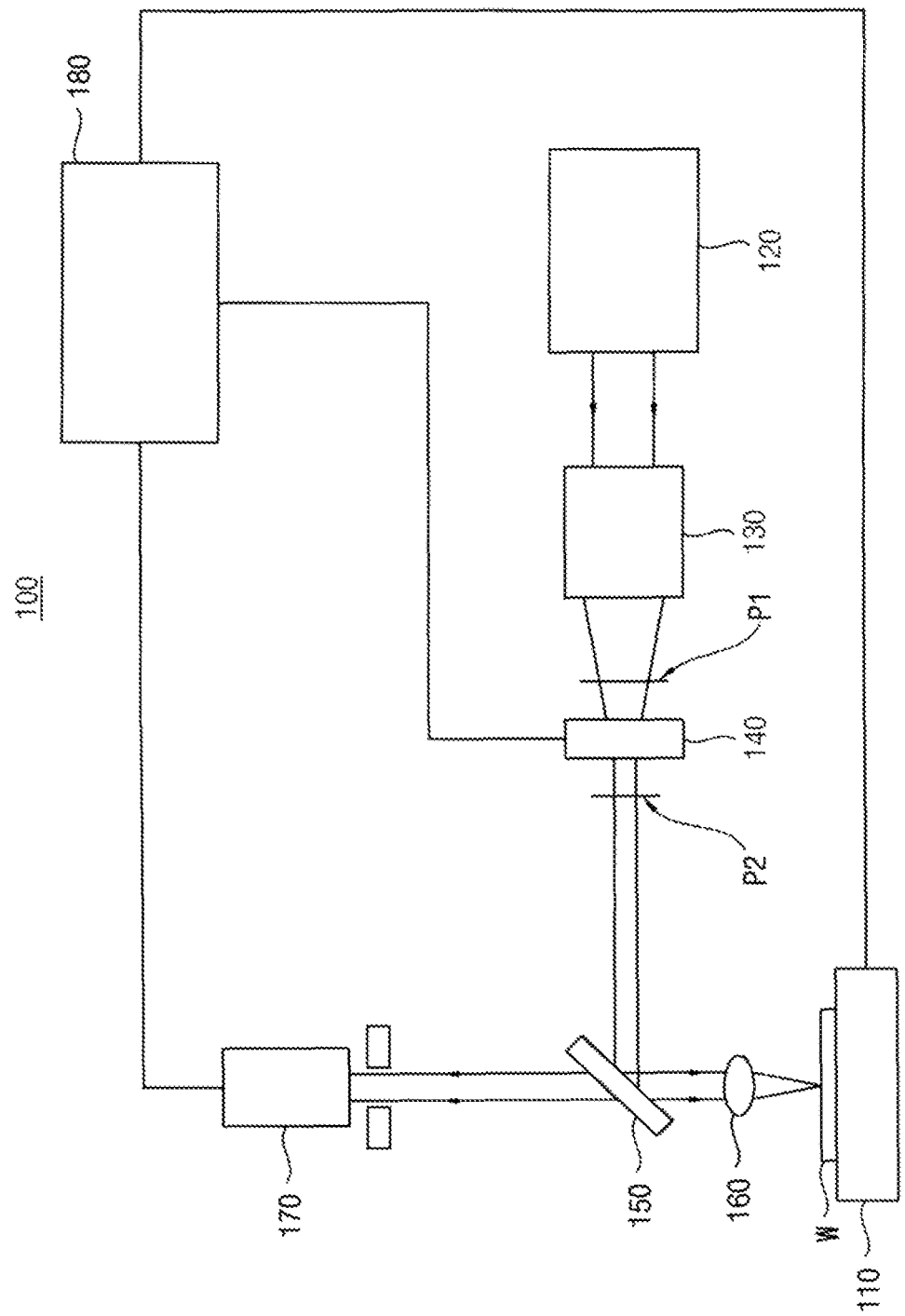
FIG. 1 is a block diagram illustrating an optical measuring apparatus according to an exemplary embodiment of the present inventive concept.

Exemplary embodiments of the present inventive concept will be described below in more detail with reference to the accompanying drawings. In this regard, the exemplary embodiments may have different forms and should not be construed as being limited to the exemplary embodiments of the present inventive concept described herein. Like reference numerals may refer to like elements throughout the specification and drawings.

Figure 2:
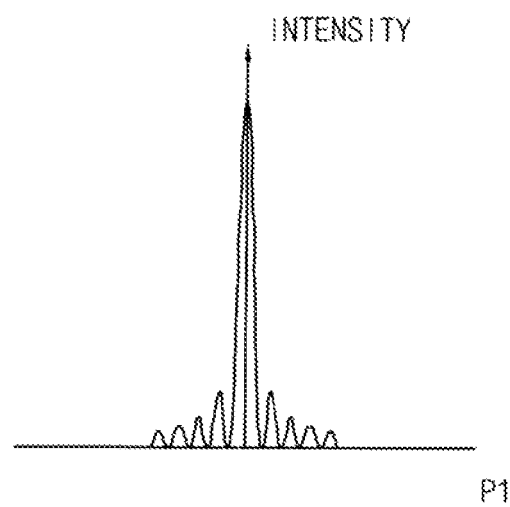
FIG. 2 is a graph illustrating an intensity profile of a Bessel beam at a P1 plane of FIG. 1 according to an exemplary embodiment of the present inventive concept.
Figure 3:
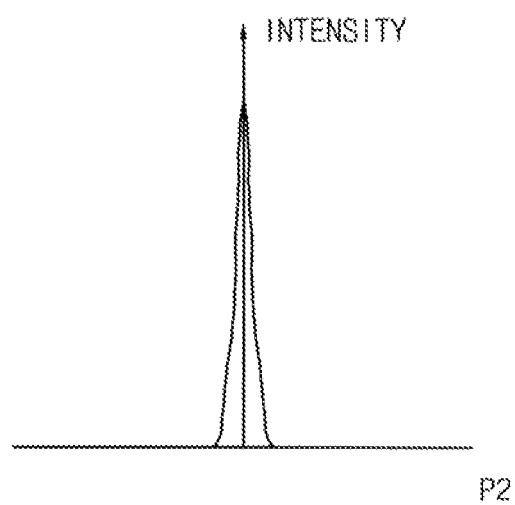
FIG. 3 is a graph illustrating an intensity profile of a modified Bessel beam at a P2 plane of FIG. 1 according to an exemplary embodiment of the present inventive concept.
Figure 4:
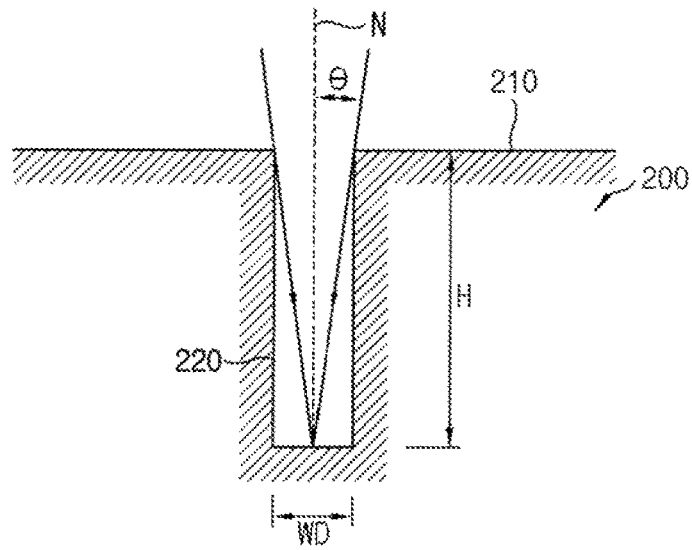
FIG. 4 illustrates an opening formed on a wafer on a stage and an incident angle of an incident beam according to an exemplary embodiment of the present inventive concept.
Figure 5:
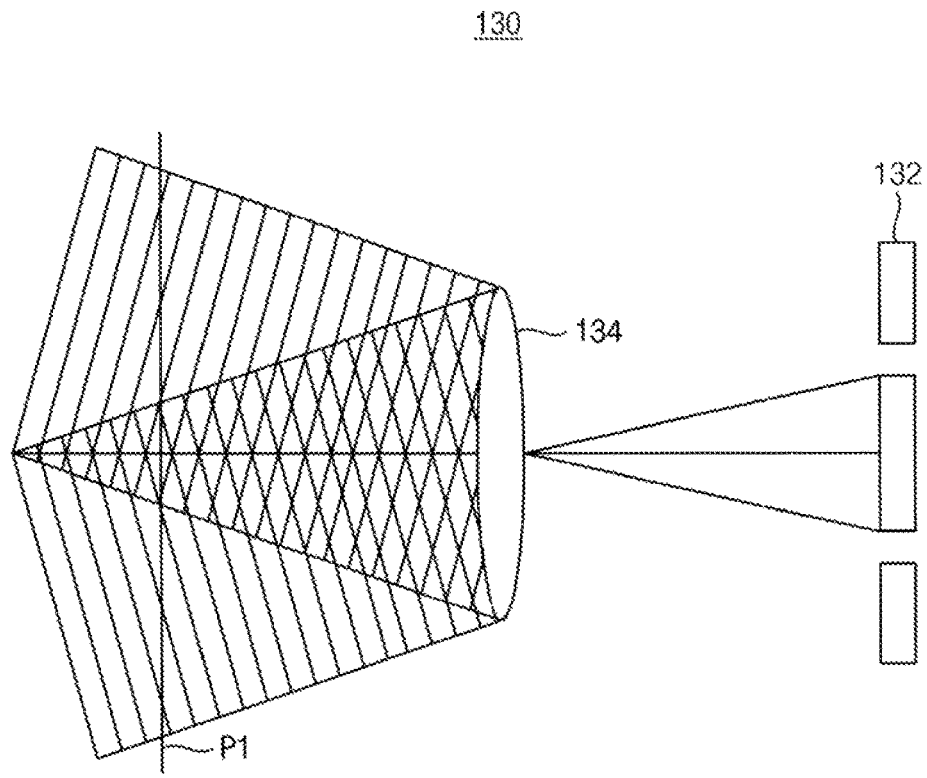
FIG. 5 is a cross-sectional view illustrating a Bessel beam generator of FIG. 1 according to an exemplary embodiment of the present inventive concept.
Figure 6:
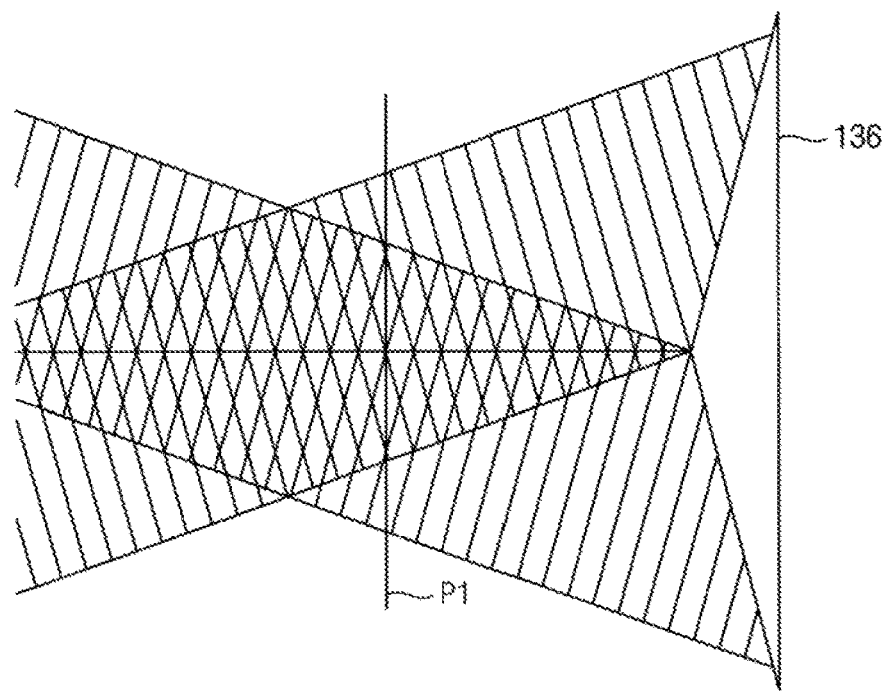
FIG. 6 is a cross-sectional view illustrating a Bessel beam generator of FIG. 1 according to an exemplary embodiment of the present inventive concept.
Figure 7:
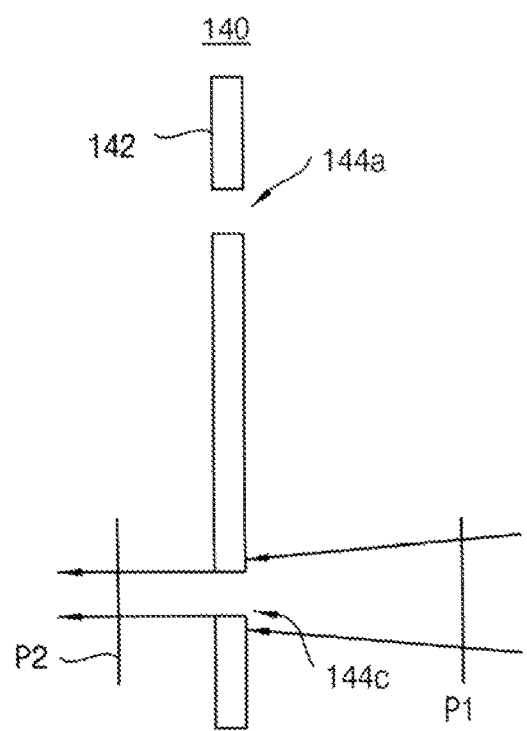
FIG. 7 is a cross-sectional view illustrating a Bessel beam adjuster of FIG. 1 according to an exemplary embodiment of the present inventive concept.
Figure 8:
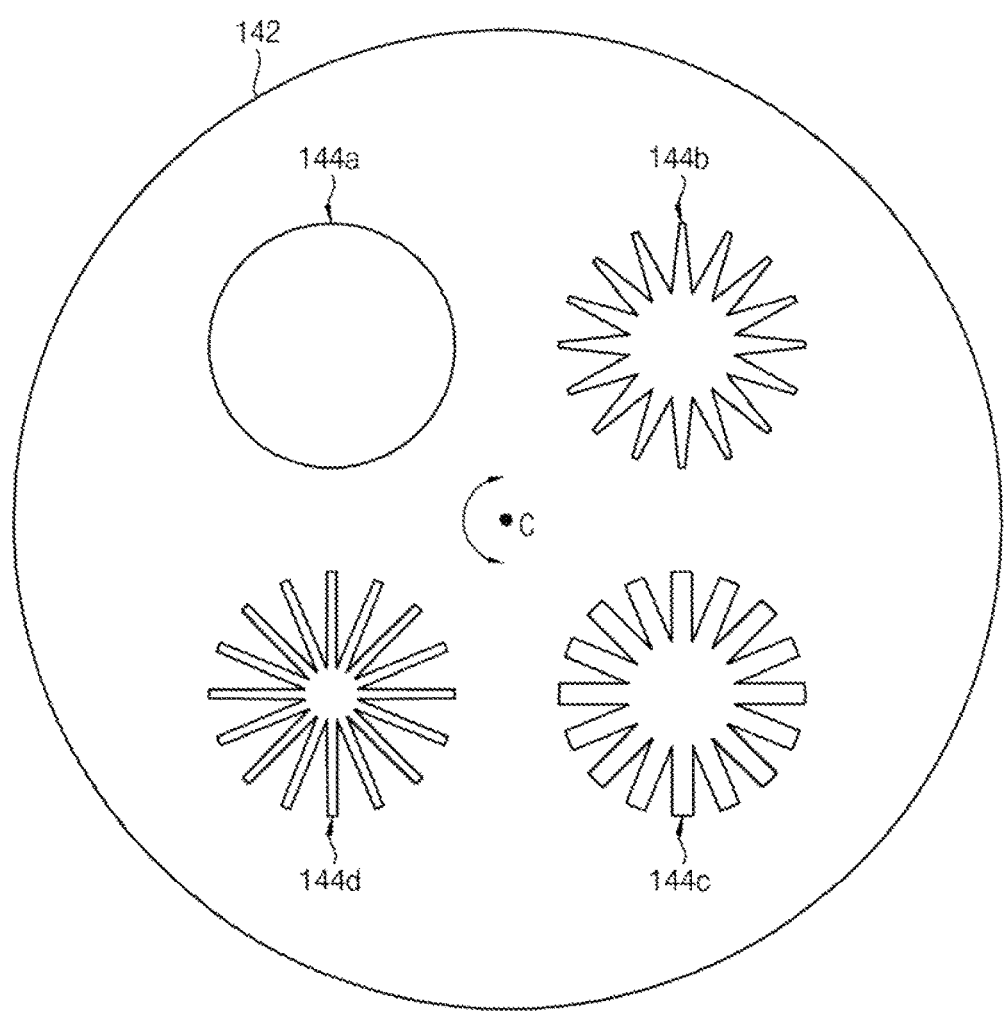
FIG. 8 is a plan view illustrating a turret-type aperture filter of the Bessel beam adjuster of FIG. 7 according to an exemplary embodiment of the present inventive concept.
Figure 9:
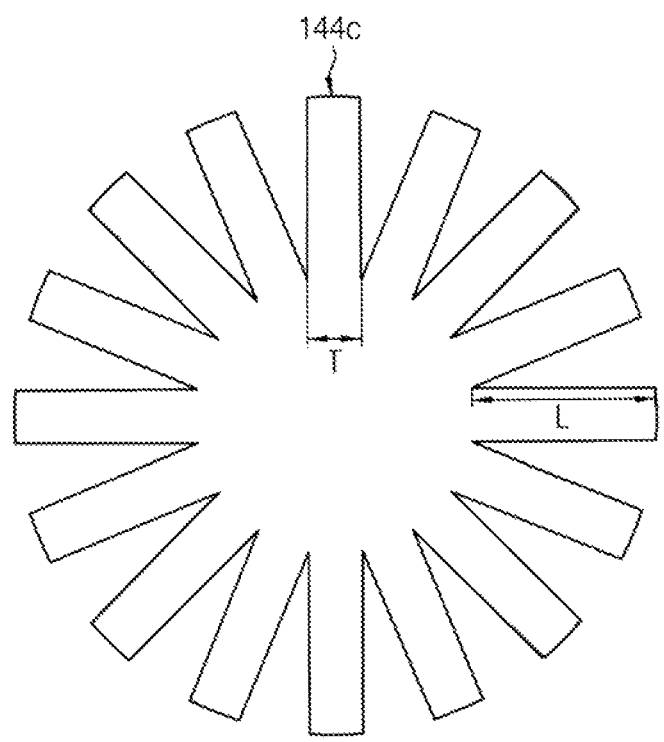
FIG. 9 is a plan view illustrating an aperture of the turret-type aperture filter of FIG. 8 according to an exemplary embodiment of the present inventive concept.
Figure 10A:
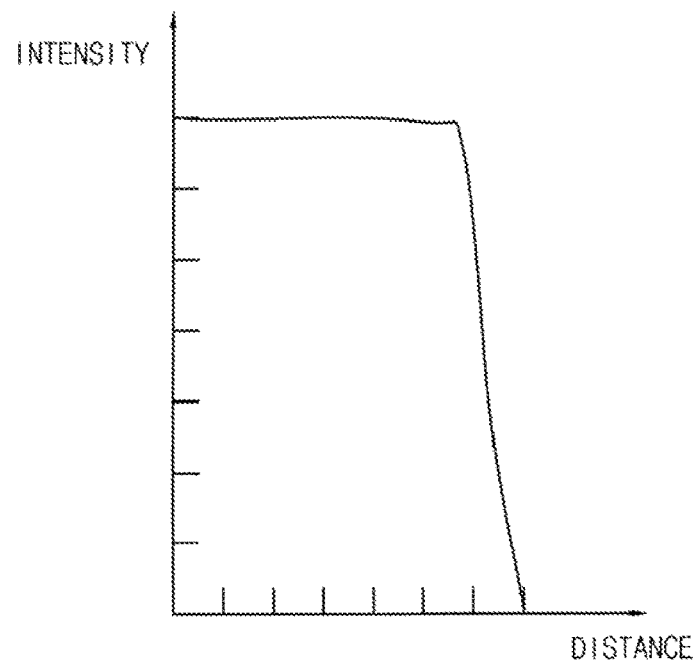
FIGS. 10A, 10B, 10C and 10D are graphs illustrating profiles of focused Bessel beams modified by apertures of the turret-type aperture filter of FIG. 8 according to an exemplary embodiment of the present inventive concept.
Figure 10B:
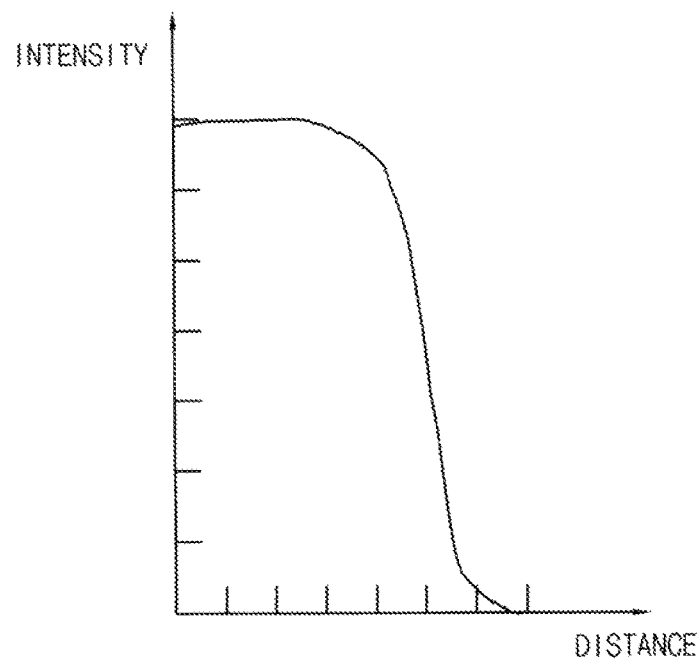
Figure 10C:
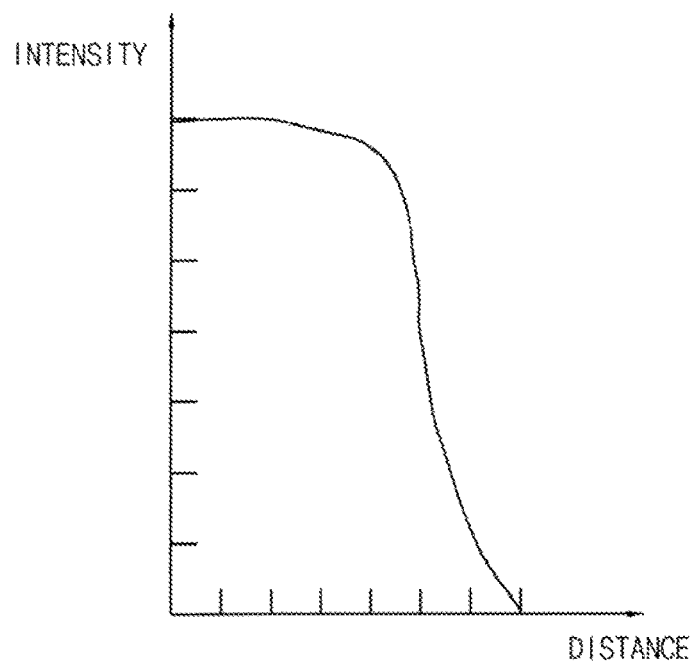
Figure 10D:
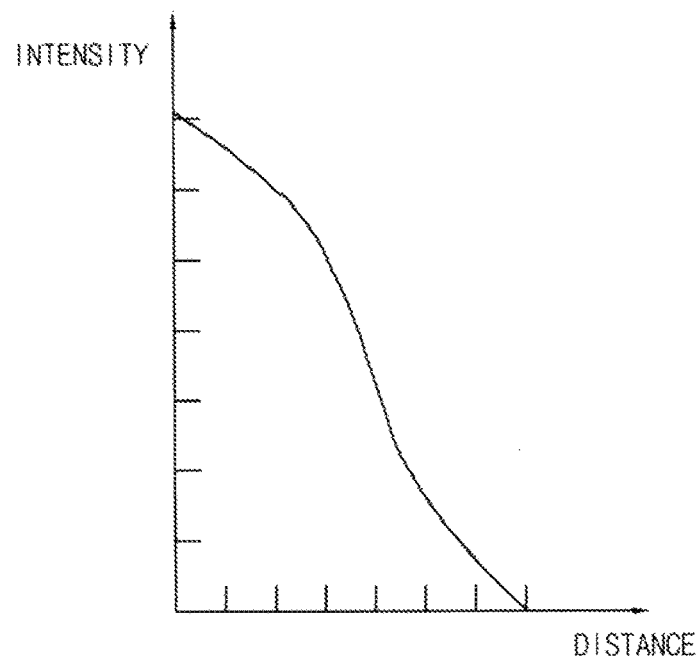
Figure 11:
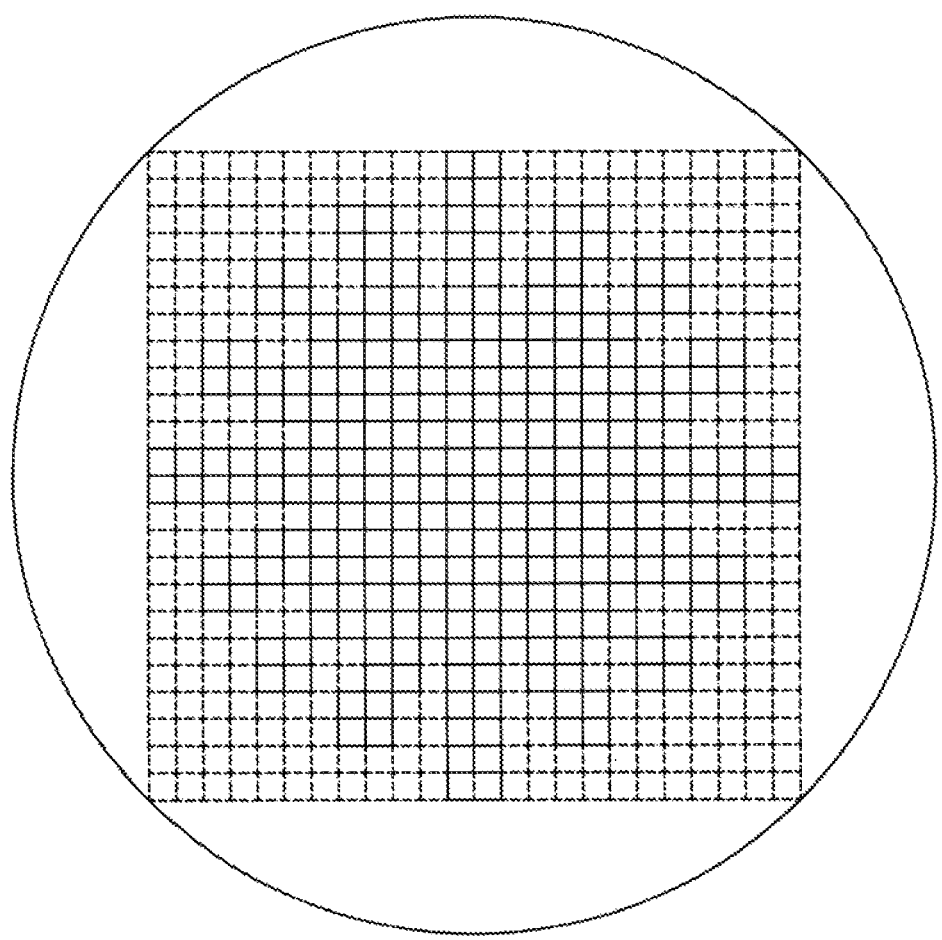
FIG. 11 is a plan view illustrating a Bessel beam adjuster of FIG. 1 according to an exemplary embodiment of the present inventive concept.
Figure 12:
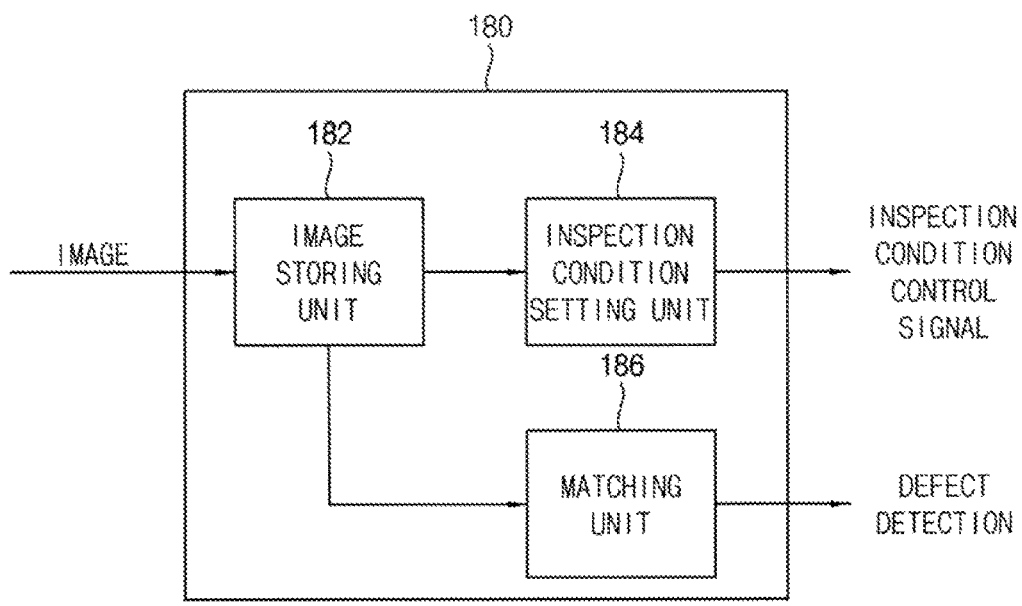
FIG. 12 is a block diagram illustrating a control unit of the optical measuring apparatus of FIG. 1 according to an exemplary embodiment of the present inventive concept.

FIG. 1 is a block diagram illustrating an optical measuring apparatus according to an exemplary embodiment of the present inventive concept. FIG. 2 is a graph illustrating an intensity profile of a Bessel beam at a P1 plane of FIG. 1 according to an exemplary embodiment of the present inventive concept. FIG. 3 is a graph illustrating an intensity profile of a modified Bessel beam at a P2 plane of FIG. 1 according to an exemplary embodiment of the present inventive concept. FIG. 4 illustrates an opening formed on a wafer on a stage and an incident angle of an incident beam according to an exemplary embodiment of the present inventive concept. FIG. 5 is a cross-sectional view illustrating a Bessel beam generator of FIG. 1 according to an exemplary embodiment of the present inventive concept. FIG. 6 is a cross-sectional view illustrating a Bessel beam generator of FIG. 1 according to an exemplary embodiment of the present inventive concept. FIG. 7 is a cross-sectional view illustrating a Bessel beam adjuster of FIG. 1 according to an exemplary embodiment of the present inventive concept. FIG. 8 is a plan view illustrating a turret-type aperture filter of the Bessel beam adjuster of FIG. 7 according to an exemplary embodiment of the present inventive concept. FIG. 9 is a plan view illustrating an aperture of the turret-type aperture filter of FIG. 8 according to an exemplary embodiment of the present inventive concept. FIGS. 10A, 10B, 10C and 10D are graphs illustrating profiles of focused Bessel beams modified by apertures of the turret-type aperture filter of FIG. 8 according to an exemplary embodiment of the present inventive concept. FIG. 11 is a plan view illustrating a Bessel beam adjuster of FIG. 1 according to an exemplary embodiment of the present inventive concept. FIG. 12 is a block diagram illustrating a control unit of the optical measuring apparatus of FIG. 1 according to an exemplary embodiment of the present inventive concept.

Referring to FIGS. 1 to 12, an optical measuring apparatus 100 may include a stage 110 dimensioned and positioned to support a substrate (e.g., a wafer W). The substrate may be a workpiece under inspection. The optical measuring apparatus 100 may include an illumination light source 120, a Bessel beam generator 130, a Bessel beam adjuster 140, an optical detector 170 and a control unit 180.

In an exemplary embodiment of the present inventive concept, the optical measuring apparatus 100 may be utilized to monitor, using a non-destructive method, a process for manufacturing semiconductor devices such as a DRAM or a vertical-type NAND memory device or semiconductor packages such as a stack chip package using a through silicon via (TSV).

For example, the optical measuring apparatus 100 may irradiate measuring light onto a wafer W in which an opening is formed and may obtain an image of a bottom surface of the opening, to detect or determine a failure or defect of the opening (e.g., a defect in a desired shape of the opening, such as a defect in the bottom surface of the opening).

The wafer W may refer to a substrate including a semiconductor or non-semiconductor material. The wafer W may include one or more layers formed thereon. For example, the one or more layers may include photoresist, a dielectric material or a conductive material; however, exemplary embodiments of the present inventive concept are not limited thereto. In an exemplary embodiment of the present inventive concept, the wafer W may include a plurality of dies each having a lattice structure of repeated patterns.

The stage 110 may support the substrate such as the wafer (W). The optical measuring apparatus 100 may include a moving mechanism for moving the stage 110. The stage 110 may be moved along a direction orthogonal to an upper surface of the stage 110 (e.g., a first direction) and/or along any direction parallel to the upper surface of the stage 110 (e.g., a second direction or a third direction). The moving mechanism may be connected to the control unit 180 and may move the stage 110 in response to a control signal input from the control unit 180. Referring to FIG. 1, a right and left direction of the stage 110 may be referred to as the second direction, a front and back direction of the stage 110 may be referred to as the third direction, and an up and down direction of the stage 110 may be referred to as the first direction.

The illumination light source 120 may generate illumination light such as a laser beam. For example, the illumination light generated from the illumination light source 120 may have a relatively short wavelength of about 266 nm or less. The illumination light may be a Gaussian beam having a Gaussian intensity profile. The illumination light source 120 may be configured to direct the illumination light to a beam splitter 150.

The Bessel beam generator 130 may be arranged in the light path of the illumination light between the illumination light source 120 and the beam splitter 150 (e.g., between the illumination light source 120 and the Bessel beam adjuster 140) to generate a Bessel beam from the illumination light. Referring to FIG. 2, the Bessel beam generated by the Bessel beam generator 130 may be a Bessel-Gauss beam having a size represented in terms of a Bessel function of a first kind. The Bessel beam may be a non-diffracting beam. A cross-section of the Bessel beam may have a circular central region at the center of a beam axis and a peripheral region including a plurality of ring-shaped regions around the central region. The circular central region may have the highest first peak and a peripheral region may have peaks having amplitudes or heights sequentially decreasing away from the beam axis In an exemplary embodiment of the present inventive concept, referring to FIG. 5, the Bessel beam generator 130 may include a diffractive optical element 132. The diffractive optical element 132 may be a ring mask with at least one annular slit and a lens 134 with a positive refractive power. The ring mask may be spaced apart from the lens 134 by one focal length. The illumination light may be directed to the diffractive optical element 132 to generate thin annular light on a back focal plane of the lens 134.

In an exemplary embodiment of the present inventive concept, referring to FIG. 6, the Bessel beam generator 130 may include an axicon lens 136. The axicon lens 136 may be a cone-shaped optical element. The illumination light having approximately a Gaussian intensity distribution across the beam axis may pass through the axicon lens 136, thus forming the Bessel beam.

The Bessel beam adjuster 140 may be arranged on the light path of the Bessel beam between the Bessel beam generator 130 and the beam splitter 150 and may filter the Bessel beam to generate a focused Bessel beam. The Bessel beam adjuster 140 may filter and limit the Bessel beam generated by the Bessel beam generator 130 to generate the focused Bessel beam. The Bessel beam adjuster 140 may be moved along the path of the Bessel beam to adjust a depth of focus (DOF) of the Bessel beam. The Bessel beam adjuster 140 may act as a spatial filter or a band pass filter.

As an example, the Bessel beam adjuster 140 may filter the peripheral region of the Bessel beam except the central region thereof to produce the focused Bessel beam. Referring to FIG. 3, the focused Bessel beam modified by the Bessel beam adjuster 140 may have a circular intensity profile with only the highest first peak.

In an exemplary embodiment of the present inventive concept, referring to FIGS. 7, 8, 9, 10A, 10B, 10C and 10D, the Bessel beam adjuster 140 may include a turret-type aperture filter 142. The turret-type aperture filter 142 may include a plurality of spaced apertures 144a, 144b, 144c and 144d therein (e.g., a plurality of spaced apertures 144a, 144b, 144c and 144d arranged in a peripheral region of the turret-type aperture filter 142). The turret-type aperture filter 142 may be configured to be rotated (e.g., by a second moving mechanism). As the turret-type aperture filter 142 rotates, the apertures 144a, 144b, 144c and 144d may also rotate. The turret-type aperture filter 142 may rotate by a predetermined angle with respect to a central axis C to select any one of the apertures 144a, 144b, 144c and 144d to filter the Bessel beam. The second moving mechanism may be connected to the control unit 180 and may rotate the turret-type aperture filter 142 in response to a control signal input from the control unit 180.

For example, at least one of the apertures 144a, 144b, 144c and 144d may have a sunburst shape (see, e.g., FIG. 8). The at least one of the apertures 144a, 144b, 144c and 144d may include radial lines that extend radially outwardly from a substantially central circular portion. The apertures 144b, 144c and 144d may include radial lines having different shapes. Referring to FIG. 9, the radial lines of the aperture 144e may each have a predetermined length L and a predetermined thickness T, for example.

FIGS. 10A, 10B, 10C and 10D illustrate intensity profiles of the Bessel beams modified by the apertures 144a, 144b, 144c and 144d, respectively. The intensity profile or noise of the Bessel beam may be modified by the length L and the thickness T of each of the radial lines of the apertures 144a, 144b, 144c and 144d. For example, as the intensity profile increases, the noise may increase. As the intensity profile decreases, the noise may be reduced.

In an exemplary embodiment of the present inventive concept, referring to FIG. 11, the Bessel beam adjuster 140 may include a spatial light modulator 146. For example, the spatial light modulator 146 may form a desired shaped aperture to filter the Bessel beam.

The beam splitter 150 may direct the modified Bessel beam (e.g., the focused Bessel beam) from the Bessel beam adjuster 140 to the wafer W on the stage 110. A refractive optical element 160 may allow the modified Bessel beam from the beam splitter 150 to focus on the wafer W. The illumination light source 120, the Bessel beam generator 130, the Bessel beam adjuster 140, the beam splitter 150 and the refractive optical element 160 may form an illumination channel.

The light that is incident to the wafer W by the illumination channel may be vertical incident light directed along the direction orthogonal to the upper surface of the wafer W. The focused Bessel beam modified by the Bessel beam adjuster 140 may have a relatively great DOF and may provide an increased resolution.

Referring to FIG. 4, an opening 220 formed in a wafer substrate 200 (e.g., the wafer W described above with reference to FIG. 1) may have a predetermined depth H from a top surface 210 thereof and a predetermined width WD. The opening 220 may have a relatively high aspect ratio. The vertical incident light may have a predetermined incident angel θ with respect to a vertical axis N along a direction orthogonal to the top surface 210 of the wafer substrate 200. For example, the vertical incident light may have the incident angle θ of about 3 degree or less. Thus, the modified Bessel beam with the relatively great DOF may reach a bottom surface of the high aspect ratio opening 220.

The light reflected from the wafer substrate 200 (e.g., from the bottom surface of the opening 220) may be collected by the refractive optical element 160 and may direct to the optical detector 170 through the beam splitter 150. The optical detector 170 may include a solid state imaging device such as a charge coupled device (CCD). At least one image may be obtained from the light reflected from the wafer substrate 200 (e.g., from the bottom surface of the opening 220) through such a detection channel.

Thus, the Bessel beam adjuster 140 may filter and limit the Bessel beam to generate the modified Bessel beam, such that a depth to which the modified Bessel beam reaches the bottom surface of the opening 220, an incident angle of the modified Bessel beam and/or single-to-noise ratio may be modified.

Referring to FIGS. 1, 4 and 12, the control unit 180 may include an image storing unit 182, an inspection condition setting unit 184 and a matching unit 186. The control unit 180 may set an inspection condition of the optical measuring apparatus 100 and may detect a defect of an inspection region, e.g., a defect on the bottom surface of the opening 220 from obtained images.

As an example, the image storing unit 182 may store detection signals or images input from the optical detector 170. The image storing unit 182 may receive and store a plurality of images related to different inspection regions (e.g., different openings formed in the wafer substrate 200) while scanning a surface of the wafer substrate 200. The images may include detection signal values corresponding to defects. Additionally, the image storing unit 182 may store a reference image related to a bottom surface of a non-defective opening.

The inspection condition setting unit 184 may select, as an inspection condition, a condition in which a reflectivity of the bottom surface of the opening 220 (e.g., an opening of a workpiece under inspection) appears to be highest from the images. A condition in which the reflectivity of the bottom surface of the opening 220 appears above a desired value among the obtained images may be selected or determined as the inspection condition.

For example, the inspection condition may include a position of the Bessel beam adjuster 140 on the path of the Bessel beam, a kind or shape of the aperture, measurement of the radial lines of the aperture and a position of the stage 110.

The inspection condition setting unit 184 may output the determined inspection condition as an inspection condition control signal to the Bessel beam adjuster 140 and the stage 110. Thus, the optical measuring apparatus 100 may obtain the images of the bottom surface of the opening 220 as the determined inspection condition, in response to the inspection condition control signal of the inspection condition setting unit 184.

The matching unit 186 may match the images to each other to detect a defect on the bottom surface of the opening 220.

For example, the matching unit 186 may match and compare an image of a bottom surface of the opening 220 to a reference image to detect the defect on the bottom surface of the opening 220. In an exemplary embodiment of the present inventive concept, the matching unit 186 may match images of bottom surfaces of adjacent openings to each other to detect any defects occurring in the adjacent openings.

As described above, the optical measuring apparatus 100 may include the Bessel beam generator 130 by which the Bessel beam is generated from the illumination light generated from the illumination light source 120 and the Bessel beam adjuster 140 that filters the Bessel beam to produce the focused Bessel beam.

The Bessel beam adjuster 140 may filter and limit the Bessel beam to generate the modified Bessel beam, such that a depth to which the modified Bessel beam reaches the bottom surface of the opening 220, an incident angle of the modified Bessel beam and single-to-noise ratio may be modified.

Thus, although the opening 220 formed in the wafer substrate 200 has the relatively high aspect ratio, the image of the bottom surface of the opening 220, that has an increased resolution, may be obtained, and also detection performance on the bottom surface of the opening 220 may be increased.

A method of measuring or inspection of an opening formed in a wafer, using the optical measuring apparatus 100 described above, and a method of manufacturing a semiconductor device using the same will be described in more detail below.

Figure 13:
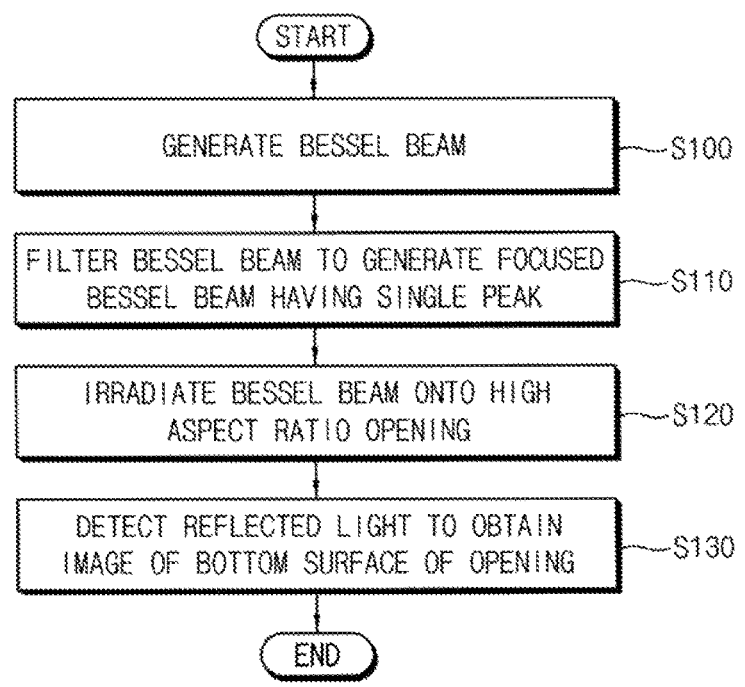
FIG. 13 is a flow chart illustrating an optical measuring method according to an exemplary embodiment of the present inventive concept.

FIG. 13 is a flow chart illustrating an optical measuring method according to an exemplary embodiment of the present inventive concept. The optical measuring method may be used to obtain an image of a bottom surface of an opening formed on a wafer by an etch process; however, exemplary embodiments of the present inventive concept are not limited thereto.

Referring to FIGS. 1 and 13, in operation S100, after the wafer W in which a high aspect ratio opening is formed is loaded on the stage 110, a Bessel beam may be generated from the illumination light generated by the illumination light source 120 using the Bessel beam generator 130.

In an exemplary embodiment of the present inventive concept, referring to FIG. 5, the Bessel beam may be generated using the lens 134 and the diffractive optical element 132 with an annular slit. In an exemplary embodiment of the present inventive concept, referring to FIG. 6, the Bessel beam may be generated using the axicon lens 136.

The Bessel beam generated by the Bessel beam generator 130 may be a Bessel-Gauss beam with a size represented in terms of a Bessel function of a first kind. The Bessel beam may be a non-diffracting beam.

In operation S110, the Bessel beam may be filtered using the Bessel beam adjuster 140 to generate a focused Bessel beam having a single peak.

In an exemplary embodiment of the present inventive concept, referring to FIGS. 7 and 8, the turret-type aperture filter 142 may be arranged on the path of the Bessel beam to filter and limit the Bessel beam. The turret-type aperture filter 142 may include a plurality of spaced apertures 144*a*, 144*b*, 144*c* and 144*d* therein. The turret-type aperture filter 142 may rotate by a predetermined angle with respect to the central axis C to select any one of the apertures 144*a*, 144*b*, 144*c* and 144*d* to filter the Bessel beam. The intensity profile or noise of the modified Bessel beam may be modified by shapes or sizes of the apertures 144*a*, 144*b*, 144*c* and 144*d*.

In an exemplary embodiment of the present inventive concept, referring to FIG. 11, the spatial light modulator 146 may be arranged on the path of the Bessel beam to adjust the Bessel beam. The spatial light modulator 146 may form a desired shaped aperture to filter the Bessel beam.

In operation S120, the focused Bessel beam may be irradiated onto a high aspect ratio opening (e.g., to a bottom surface of the opening formed in the wafer W), as incident light directed along a direction orthogonal to an upper surface of the wafer W. In operation S130, light reflected from the high aspect ratio opening in the wafer W may be detected to obtain an image of a bottom surface of the high aspect ratio opening.

In an exemplary embodiment of the present inventive concept, the Bessel beam modified from the Bessel beam adjuster 140 may be directed to the wafer W on the stage 110 by the beam splitter 150.

The light irradiated onto the wafer W nay be vertical incident light.

The vertical incident light may have a predetermined incident angle θ with respect to a vertical axis N orthogonal to a top surface of the wafer W (see, e.g., FIG. 4). For example, the vertical incident light may have the incident angle θ of about 3 or less to the vertical axis. Thus, the modified focused Bessel beam with a great DOF may reach the bottom surface of the high aspect ratio opening.

The light reflected from the bottom surface of the high aspect ratio opening may be collected by the refractive optical element 160 and may direct to the optical detector 170 through the beam splitter 150. The optical detector 170 may include a solid state image device such as a charge coupled device, and thus may obtain an image from the light reflected from the bottom surface of the high aspect ratio opening.

The obtained image may be analyzed to detect whether or not a defect is present on the bottom surface of the high aspect ratio opening.

A method of manufacturing a semiconductor device using the optical measuring method described with reference to FIG. 13 will be described in more detail below.

Figure 14:
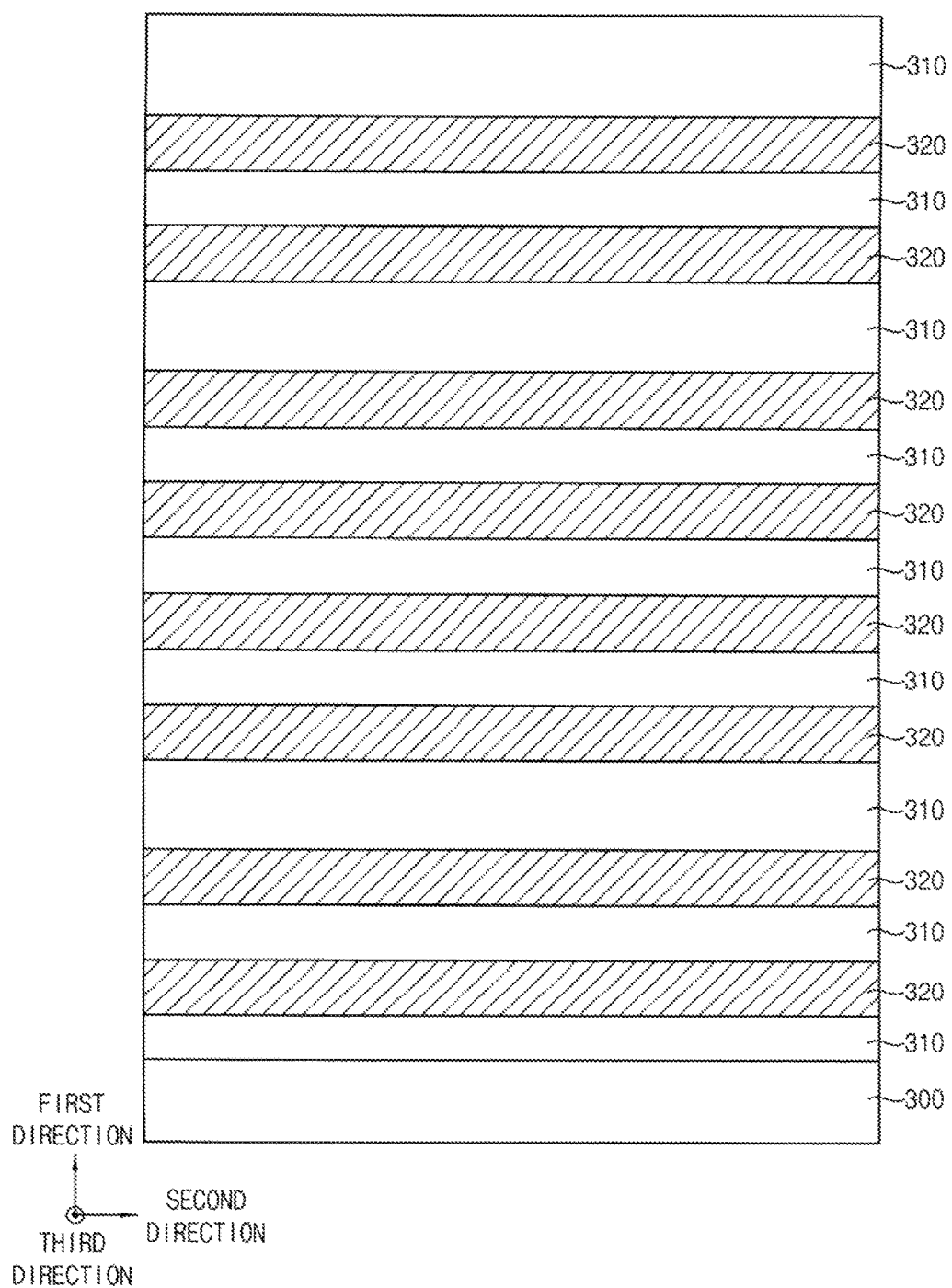
FIGS. 14 to 16 are cross-sectional views illustrating a method of manufacturing a vertical-type memory device according to an exemplary embodiment of the present inventive concept.
Figure 15:
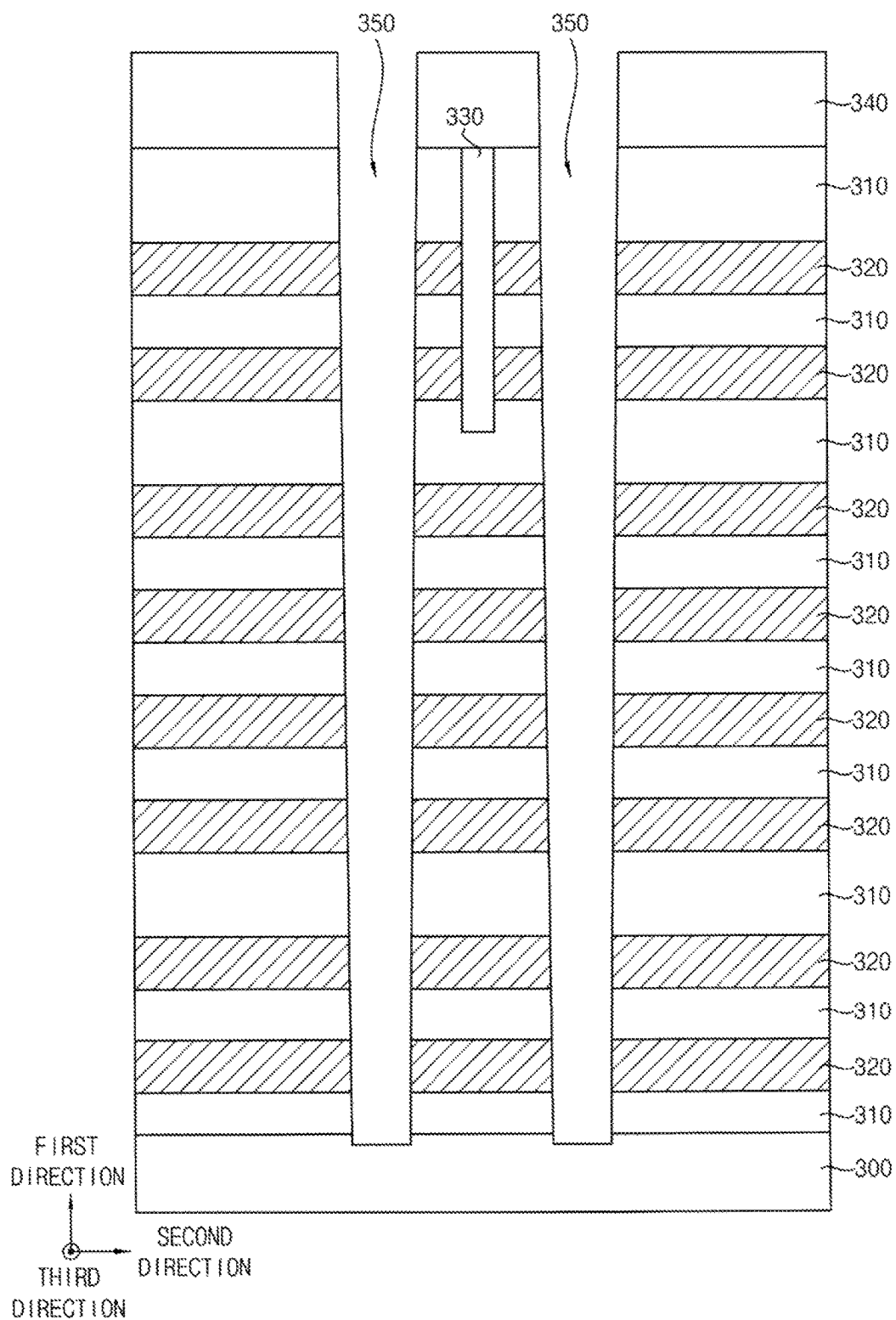
Figure 16:
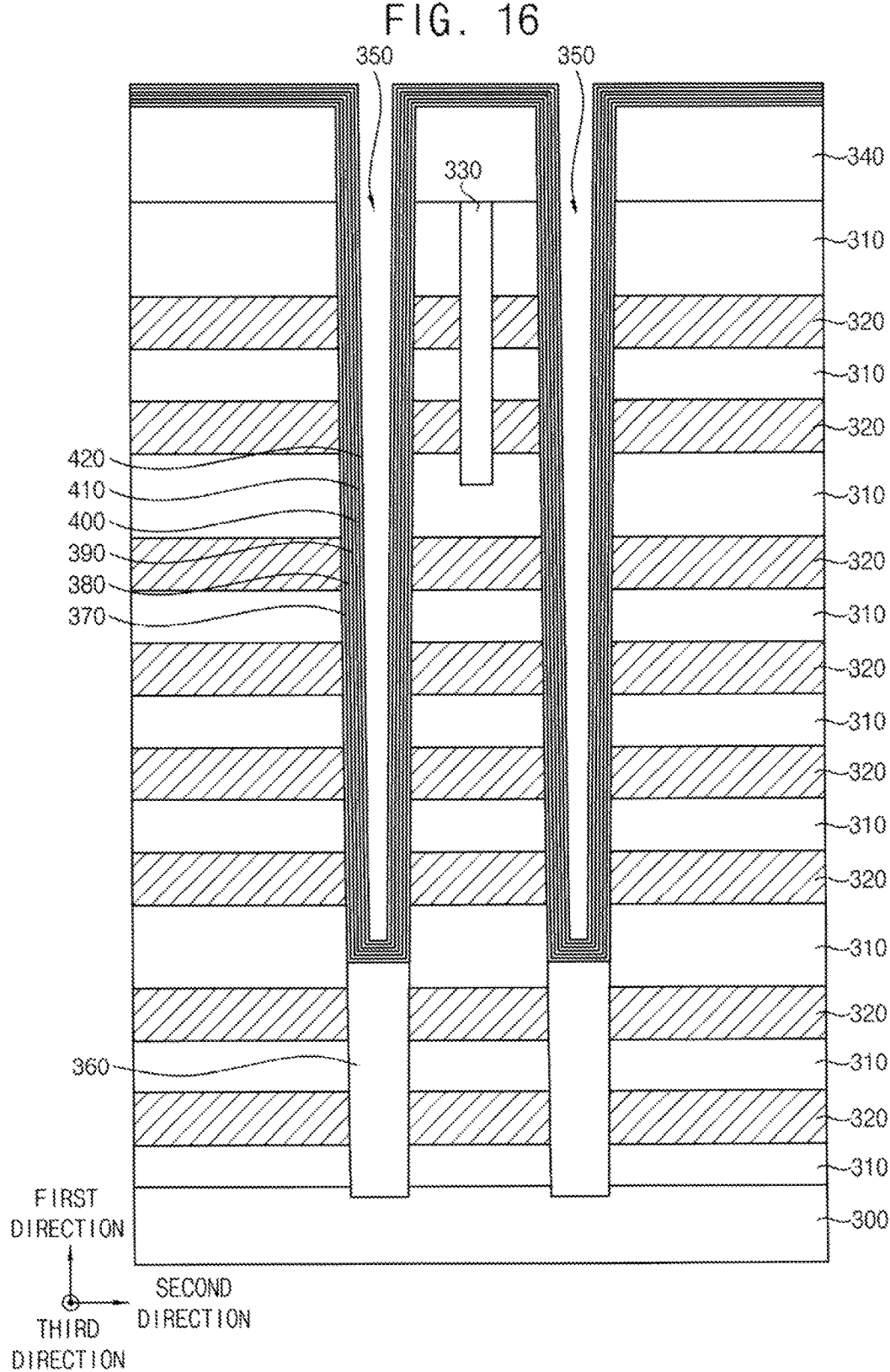

FIGS. 14 to 16 are cross-sectional views illustrating a method of manufacturing a vertical-type memory device according to an exemplary embodiment of the present inventive concept. Referring to FIGS. 14 to 16, a direction orthogonal to a top surface of a wafer substrate 300 (the wafer W described, e.g., with reference to FIG. 1) may be referred to as a first direction and directions parallel to the top surface of the wafer substrate 300 and perpendicular to each other may be referred to as a second direction and a third direction.

Referring to FIG. 14, first insulating layers 310 and sacrificial layers 320 may be alternately and repeatedly stacked on the wafer substrate 300 in the first direction. The wafer substrate 300 may include a semiconductor material such silicon or germanium.

In an exemplary embodiment of the present inventive concept, the first insulating layers 310 and the sacrificial layers 320 may be formed by a chemical vapor deposition (CVD) process, a plasma enhanced CVD process or an atomic layer deposition (ALD) process.

The first insulating layers 310 may include an oxide. The sacrificial layers 320 may include a material having an etching selectivity with respect to the first insulating layers 310, e.g., silicon nitride.

Referring to FIG. 15, a plurality of openings 350 may pass through the first insulating layers 310 and the sacrificial layers 320 to expose the top surface of the wafer substrate 300. An insulating layer 330 may be formed to partially penetrate the first insulating layers 310 and the sacrificial layers 320. The insulating layer 330 may be formed before forming the openings 350.

In an exemplary embodiment of the present inventive concept, the openings 350 may be formed by forming a mask layer 340 on an uppermost one of the first insulating layers 310 and performing a dry etch process using the mask layer 340 as an etch mask. The openings 350 may each be formed to extend in the first direction. Due to characteristics of the dry etch process, the openings 350 may each be formed to narrow downward.

An image of a bottom surface of each of the openings 350 having a high aspect ratio may be obtained by using the optical measuring method described with reference to FIGS. 1 to 13 above, thus monitoring the etch process.

In an exemplary embodiment of the present inventive concept, after loading the wafer substrate 300, on which the high aspect ratio openings 350 are formed, on the stage 110 of the optical measuring apparatus 100, the focused Bessel beam may be irradiated onto the wafer substrate 300 and then the light reflected from the bottom surfaces of the openings 350 may be detected to detect whether or not defects are present on the bottom surfaces of the openings 350.

As an example, the Bessel beam modified from the Bessel beam adjuster 140 may be directed to irradiate the wafer substrate 300 on the stage 110 through the beam splitter 150. The light that is incident to the wafer substrate 300 may be vertical incident light.

The vertical incident light may have a predetermined incident angle with respect to a vertical axis perpendicular to the top surface of the wafer substrate 300 (see, e.g., FIG. 4). The vertical incident light may have the incident angle of about 3 degrees or less. Thus, the modified Bessel beam with a great DOF may reach the bottom surface of each of the high aspect ratio openings 350

The light reflected from the bottom surfaces of the high aspect ratio openings 350 may be collected by the refractive optical element 160 and may direct to the optical detector 170 through the beam splitter 150. The optical detector 170 may obtain images from the light reflected from the bottom surfaces of the high aspect ratio openings 350. The obtained images may be analyzed to detect whether or not defects are present on the bottom surfaces of the high aspect ratio openings 350.

Referring to FIG. 16, after forming a semiconductor pattern 360 partially filling each of the high aspect ratio openings 350, a first blocking layer 370, a charge storage layer 380, a tunnel insulating layer 390, a first channel layer 400, an etch stopper layer 410 and a spacer layer 420 may be sequentially formed on inner surfaces of the high aspect ratio openings 350, a top surface of the semiconductor pattern 360 and a top surface of the mask layer 340.

The semiconductor pattern 360 may be formed by a selective epitaxial growth process using the top surface of the wafer substrate 300 exposed by the high aspect ratio openings 350 as a seed to partially fill each of the high aspect ratio openings 350.

The first blocking layer 370, the charge storage layer 380 and the tunnel insulating layer 390 may be sequentially formed on the wafer substrate 300 with a substantially uniform thickness by, e.g., an ALD process.

Thereinafter, a first blocking pattern, a charge storage pattern, a tunnel insulating pattern, a channel and a second insulating pattern may be formed on the semiconductor pattern 360 in each of the high aspect ratio openings 350. The sacrificial layers 320 may be removed, and then gate electrodes (e.g., a ground selection line, word lines and a string selection line) that are sequentially formed in the first direction from the top surface of the wafer substrate 300 may be formed. Bit lines may be formed on a resultant structure having the gate electrodes. Thus, the vertical type memory device may be fabricated as described above.

The semiconductor device such as the DRAM or the vertical-type NAND memory device or the semiconductor package such as the stack chip package using the TSV formed by the optical measuring or metrology method and the optical measuring or metrology apparatus according to an exemplary embodiment of the present inventive concept may be applied to a system such as a computing system. The system may include a computer, a mobile computer, a laptop computer, a personal computer, a tablet, a mobile phone, or a digital music player.

While the present inventive concept has been particularly shown and described with reference to exemplary embodiments thereof, it will be understood by those of ordinary skill in the art that various changes in form and details may be made therein without departing from the spirit and scope of the present inventive concept.

What is claimed is:

1. An optical measuring method comprising:
    generating a Bessel beam using a Bessel beam generator;
    filtering the generated Bessel beam through an aperture filter to generate a focused Bessel beam;
    directing the focused Bessel beam into an opening formed in a substrate along a direction orthogonal to an upper surface of the substrate; and
    detecting the focused Bessel beam light reflected from a bottom surface of the opening to obtain an image of the bottom surface of the opening,
    wherein the aperture filter is disposed between the Bessel beam generator and a stage for a substrate, and
    wherein generating the Bessel beam includes:
    generating a Gaussian beam; and
    passing the Gaussian beam through the Bessel beam generator in a path of the Gaussian beam to generate the Bessel beam.

2. The method according to claim 1, wherein the Bessel beam generator includes a diffractive optical element including an annular slit and a lens, or an axicon lens.

3. The method according to claim 1, wherein generating the focused Bessel beam includes filtering a peripheral region of the Bessel beam, and transmitting a central region of the Bessel beam to generate the focused Bessel beam having a single peak.

4. The method according to claim 1, wherein generating the focused Bessel beam includes passing the Bessel beam through a Bessel beam adjuster in a path of the Bessel beam to filter the Bessel beam.

5. The method according to claim 4, wherein the Bessel beam adjuster includes a turret-type aperture filter including a plurality of apertures.

6. The method according to claim 5, wherein at least one of the plurality of apertures has a sunburst shape.

7. The method according to claim 5, wherein the Bessel beam adjuster is configured to move along the path of the Bessel beam.

8. The method according to claim 4, wherein the Bessel beam adjuster includes a spatial light modulator.

9. The method according to claim 1, wherein the focused Bessel beam that is directed into the opening formed in the substrate has an incident angle of 3 degree or less with respect to a vertical axis orthogonal to the upper surface of the substrate.

10. A method of manufacturing a semiconductor device, comprising
    providing a wafer including an opening;
    generating a Bessel beam;
    filtering the Bessel beam to generate a focused Bessel beam;
    directing the focused Bessel beam into the opening along a direction orthogonal to an upper surface of the wafer;
    detecting light reflected from the wafer to obtain an image of a bottom surface of the opening; and
    analyzing the obtained image to detect a defect of the opening by comparing the obtained image with a reference image, wherein a height of the opening is greater than a width of the opening.

11. The method according to claim 10, wherein generating the focused Bessel beam includes filtering a peripheral region of the Bessel beam except a central region thereof to generate the focused Bessel beam having a single peak.

12. The method according to claim 10, wherein generating the focused Bessel beam includes passing the Bessel beam through an aperture filter in a path of the Bessel beam to filter the Bessel beam.

13. The method according to claim 12, wherein the aperture filter is configured to move along the path of the Bessel beam.

14. The method according to claim 10, further comprising depositing at least one material layer in the opening to fill at least a portion of the opening.

15. The method according to claim 1, wherein the Bessel beam generated is a Bessel-Gauss beam.

16. The method according to claim 1, further comprising:
   generating an illumination light by using an illumination light source;
      passing the illumination light through the Bessel beam generator to generate the generated Bessel beam; and
      forming a light channel by arranging the illumination light source, the Bessel beam generator and the aperture filter on a substantially same plane.

17. The method according to claim 1, wherein the stage is movable by a control unit, wherein said control unit is also connected to the aperture filter and an optical detector.

\* \* \* \* \*